United States Patent [19]

Takami et al.

[11] 4,279,917

[45] Jul. 21, 1981

[54] AMINO ACID SOLUTION FOR INTRAVENOUS NUTRITION

[75] Inventors: Toru Takami, Yokosuka; Yuriko Yonekawa, Kashiwa, both of Japan

[73] Assignee: Ajinomoto Company, Incorporated, Tokyo, Japan

[21] Appl. No.: 72,670

[22] Filed: Sep. 5, 1979

[30] Foreign Application Priority Data

Sep. 8, 1978 [JP] Japan ................... 53-110892

[51] Int. Cl.³ ................. A61K 31/415; A61K 31/40; A61K 31/195

[52] U.S. Cl. ............................ 424/273 R; 424/274; 424/319

[58] Field of Search ............ 424/180, 319, 177, 273 R, 424/274

[56] References Cited

U.S. PATENT DOCUMENTS

| | | | |
|---|---|---|---|
| 2,411,897 | 12/1946 | Sahyun | 424/319 |
| 3,080,234 | 5/1963 | Jarowski | 424/319 |
| 3,697,287 | 10/1972 | Winitz | 424/319 |
| 3,773,930 | 11/1973 | Mohammed et al. | 424/180 |
| 3,832,465 | 8/1974 | Ghodimi | 424/273 |
| 3,920,838 | 11/1975 | Flatt et al. | 424/319 |
| 3,950,529 | 4/1976 | Fischer et al. | 424/319 |
| 4,003,992 | 1/1977 | Beigler et al. | 424/319 |
| 4,009,265 | 2/1977 | Howard | 424/180 |
| 4,085,207 | 4/1978 | Aoki et al. | 424/180 |

*Primary Examiner*—Delbert R. Phillips
*Assistant Examiner*—Blondel Hazel
*Attorney, Agent, or Firm*—Oblon, Fisher, Spivak, McClelland & Maier

[57] ABSTRACT

An amino acid intravenous solution is provided which comprises an aqueous solution of L-isoleucine, L-leucine, L-lysine, L-methionine, L-phenylalanine, L-threonine, L-tryptophan, L-valine, L-cystine, L-tyrosine, L-alanine, L-arginine, L-aspartic acid, L-glutamic acid, glycine, L-histidine, L-proline and L-serine wherein all or a portion of the cystine component can be substituted by cysteine and/or methionine, while all or a portion of the tyrosine can be substituted by phenylalanine.

3 Claims, No Drawings

AMINO ACID SOLUTION FOR INTRAVENOUS NUTRITION

BACKGROUND OF THE INVENTION

1. Field of the Invention

The present invention relates to a nutritious amino acid solution for intravenous feeding, particularly for those patients who have undergone a surgical operation.

2. Description of the Prior Art

From the viewpoint of nutrition and physiology, the compositions of currently used amino acid infusion solutions have need for much improvement. First of all, the compositions of commercially available solutions are based upon the knowledge of oral nutrition requirements. Thus, some typical commercial amino acid based infusion solutions have been formulated based upon the essential amino acid requirements recommended by FAO, or have been based upon a knowledge of the amino acid composition of human milk. Secondly, if an intravenous composition is not based upon oral nutrition requirements, it then is probably based upon the amino acid requirements for a healthy person, for example, the plasma free amino acid pattern of human subjects.

Generally, an amino acid infusion solution is administered intravenously to a patient who has undergone a surgical operation. Thus, the composition of the solution should be such that it is utilized most effectively when administered parenterally to patients with pathological conditions. Preferably, for such people an intravenous composition should not be used which is the same as that used for oral administration or as a composition formulated in view of the nutritional requirements of a healthy person. The reason for this is as follows. Orally administered amino acids are absorbed in the small intestine, and are then passed throughout and utilized by the body. The initial composition is modified by bacteria initiated decomposition in the small intestine followed by competitive absorption of such amino acids as valine, leucine and isoleucine in the small intestine. Thereafter, enzymatic metabolism of the amino acid occurs in the liver and so on. On the other hand, for an infusion solution which is directly supplied to the tissues of the body by injection of the infusion solution into the blood in a vein which is circulated by the blood, no change in composition of the infusion occurs upon parenteral administration. For these reasons, the optimal composition for an amino acid solution administered by infusion should be different from that administered orally.

Moreover, it is known that patients suffering from different pathological conditions show different metabolic capacities. Accordingly, the amino acid nutritional requirements for patients in different pathological states vary as disclosed by P. M. Sender et al in "Nutritional Aspects of Care in the Critically Ill", 1977, edited by J. R. Richards et al, Churchill Livingstone, page 177.

In order for an amino acid based infusion solution to be more effective from the viewpoint of nutritional physiology, the amino acid infusion solution should have a composition which meets the amino acid requirements of patients under a particular pathological state in order to keep up a normal pool of amino acids in the living body. Thus, the composition of the infusion should be selected so as to compensate for the changes which occur in amino acid metabolism in a living body under a given pathological state, and to normalize the amino acid pattern in the blood, by supplying such a solution which is truly effective from the viewpoint of nutritional physiology. It should be observed that, strictly speaking, the metabolic changes which occur for a given pathological condition and the mode of correction or normalization also vary according to the specie of animal suffering from the condition. The variations in the amino acid metabolism of man and rat are not quantitatively the same, although they show similar qualitative tendencies. Thus, it might be concluded that a composition proven to be effective for a rat or a dog might not be effective for a man. However, such compositions are far more preferred in comparison to infusion compositions which are based on oral nutrition requirements. Therefore, a need has continued to exist for infusion solutions of compositions more appropriate for patients who have undergone surgical operations and are in a given pathological state.

SUMMARY OF THE INVENTION

Accordingly, one object of the present invention is to provide an intravenous infusion composition formulated specifically for patients in a given pathological state.

Breifly, this object and other objects of the present invention as hereinafter will become more readily apparent can be attained by an amino acid based infusion solution of the following composition:

| Amino Acids | Mole % |
| --- | --- |
| L-isoleucine | 6.95–7.69 |
| L-leucine | 15.36–16.98 |
| L-lysine | 3.36–3.72 |
| L-methionine | 1.06–1.18 |
| L-phenylalanine | 7.99–8.83 |
| L-threonine | 7.74–8.56 |
| L-tryptophan | 1.71–1.89 |
| L-valine | 16.35–18.07 |
| L-cystine | 2.28–2.52 |
| L-tyrosine | 0.25–0.27 |
| L-alanine | 4.22–4.66 |
| L-arginine | 5.03–5.55 |
| L-aspartic acid | 0.66–0.72 |
| L-glutamic acid | 0.40–0.44 |
| glycine | 11.58–12.80 |
| L-histidine | 3.85–4.25 |
| L-proline | 4.77–5.27 |
| L-serine | 1.39–1.53 | wherein all or a portion of the cystine can be substituted by cysteine and/or methionine, and all or a portion of the tyrosine can be substituted by phenylalanine.

DETAILED DESCRIPTION OF THE PREFERRED EMBODIMENTS

In the study leading to the present invention a rat whose small intestine had been surgically removed was used as a model for a post-operative patient. An investigation was conducted for observing changes in amino acid metabolism which occur in this model by analyzing plasma amino acid patterns. Thereafter, an amino acid infusion solution (S-5) was formulated which had a composition capable of correcting the metabolic changes resulting from the resection of the small intestine and the efficacy of the (S-5) solution on the rat as the infusion solution was ascertained. Then, the variations in the amino acid metabolism of a post-operative patient were investigated by measuring the amino acid pattern of the blood plasma. From this information it was ascertained that the metabolic changes which occur in post-operative human patients are qualitatively similar to those which appear in the model rats which are under a post-operative condition. However, it became apparent that the changes were not quantitatively the same because of the difference in species between man and rat. Thus, a correction attributable to this difference was made to formulate an amino acid solution (H-5) which has an efficient composition for man under a post-operative state.

The ileum of a male Wistar rat weighing 300 g had been resected while under anesthesia by one third of the whole length of the small intestine, and the resected ends were anastomosed together. For the rat which had undergone the operation the plasma amino acid pattern was analyzed at 6, 24, 48 and 72 hours after the operation by using an Hitachi automatic amino acid analyzer. As it turned out as shown in Table 1, remarkable variations in amino acid patterns were observed from the normal values 24 to 48 hours, and especially 48 hours after the operation. It was shown that the nitrogen balance, hematocrit values and the total protein in the blood were lower than their normal values, and that remarkable changes occurred in the amino acid metabolism. Among the amino acid components of the blood, valine, leucine, isoleucine, phenylalanine, tyrosine, arginine and histidine increased in amounts above their normal values, while alanine, ornithine, citrulline, proline and lysine decreased. These data indicate that the required amounts for a given amino acid in the living body change when the body has undergone an operation.

TABLE 1

AMINO ACID CONCENTRATIONS IN RAT BLOOD
48 Hours After Operation (μmoles/dl)

|  | Operated Group | Control Group |
| --- | --- | --- |
| isoleucine | 8.94 ± 0.78 | 5.90 ± 0.51 |
| leucine | 18.43 ± 6.65* | 11.21 ± 0.09* |
| lysine | 28.84 ± 3.29 | 36.49 ± 1.69 |
| methionine | 5.58 ± 0.53 | 5.09 ± 0.20 |
| phenylalanine | 8.70 ± 1.25* | 4.69 ± 0.12* |
| tryptophan | 5.43 ± 0.69 | 5.59 ± 0.36 |
| valine | 21.60 ± 8.29 | 14.29 ± 0.11 |
| cystine | 0.995 ± 0.25 | 0.63 ± 0.09 |
| tyrosine | 6.59 ± 1.50 | 5.75 ± 0.60 |
| alanine | 36.90 ± 5.38 | 43.83 ± 2.71 |
| arginine | 9.91 ± 0.36 | 7.46 ± 4.39 |
| aspartic acid | 1.27 ± 0.44 | 1.73 ± 0.81 |
| citrulline | 4.02 ± 0.38* | 5.72 ± 0.28* |
| glutamic acid | 8.81 ± 1.41 | 12.08 ± 1.72 |
| glycine | 25.32 ± 2.46 | 25.19 ± 1.39 |
| histidine | 7.34 ± 1.44 | 5.66 ± 0.07 |
| hydroxyproline | 2.80 ± 0.57 | 3.74 ± 0.10 |
| ornithine | 3.35 ± 1.12* | 11.28 ± 3.82* |
| proline | 8.11 ± 0.91* | 15.53 ± 1.04* |
| serine | 23.17 ± 2.32 | 24.00 ± 0.15 |
| taurine | 15.58 ± 4.26 | 15.76 ± 1.14 |

*p < 0.05

In a similar manner, the amino acid pattern was investigated for a man in a post-operative state 24 and 72 hours after the operation. Similar to the situation above, remarkable variations in blood amino acid patterns occurred 72 hours after the operation as shown in Table 2. Among the amino acids which vary as a result of the operation on the human patient are valine, leucine, isoleucine, phenylalanine and tyrosine which increased in their amounts, while alanine, ornithine, citrulline, proline and glycine decreased. Such variations have turned out to be quite similar to those observed in rats as shown in Table 3. Thus, it may be said that the changes in amino acid metabolism caused by the operation show similar tendencies in both the human patient and the rat model. In other words, the changes in the amounts of the amino acid components required by the living body are qualitatively similar in both man and rat. Thus, the composition of the amino acid solution obtained based on the results of the experiments on rats can obviously be translated to that for the human patient with some quantitative corrections.

TABLE 2

AMINO ACID CONCENTRATIONS IN HUMAN BLOOD
72 Hours After Operation (μmoles/dl)

|  | Before Operation | 72 Hours After Operation |
| --- | --- | --- |
| isoleucine | 5.75 ± 1.21 | 7.05 ± 1.37* |
| leucine | 9.99 ± 2.55 | 13.73 ± 2.28* |
| lysine | 18.92 ± 3.45 | 18.34 ± 3.88 |
| methionine | 2.33 ± 0.58 | 2.80 ± 1.05 |
| phenylalanine | 4.97 ± 1.04 | 6.42 ± 0.64* |
| tryptophan | 4.71 ± 2.64 | 4.46 ± 2.08 |
| valine | 18.32 ± 5.90 | 19.86 ± 5.83 |
| cystine | 4.19 ± 1.53 | 4.64 ± 1.26 |
| tyrosine | 5.50 ± 1.35 | 6.23 ± 0.92 |
| alanine | 27.23 ± 7.31 | 21.46 ± 3.18* |
| arginine | 8.44 ± 1.77 | 6.56 ± 1.34* |
| aspartic acid | 0.61 ± 0.48 | 0.50 ± 0.19 |
| citrulline | 2.60 ± 0.92 | 1.64 ± 0.33* |
| glutamic acid | 6.25 ± 1.28 | 6.80 ± 1.28 |
| glycine | 17.74 ± 5.57 | 14.90 ± 2.80 |
| histidine | 7.71 ± 1.33 | 6.48 ± 1.11* |
| ornithine | 8.72 ± 3.33 | 6.92 ± 3.01 |
| proline | 9.58 ± 2.64 | 8.45 ± 1.42 |
| serine | 13.12 ± 2.77 | 14.39 ± 2.64 |
| taurine | 2.95 ± 2.01 | 2.49 ± 0.87 |

*p < 0.05

TABLE 3

VARIATIONS IN THE AMOUNTS OF AMINO ACID
COMPONENTS IN THE BLOOD OF THE RAT
AND MAN AFTER OPERATION

|  | Rat | Man |
| --- | --- | --- |
| Amino acids which increase after operation | valine<br>leucine<br>isoleucine<br>phenylalanine<br>tyrosine<br>arginine<br>histidine | valine<br>leucine<br>isoleucine<br>phenylalanine<br>tyrosine |
| Amino acid which decrease after operation | alanine<br>ornithine<br>cirtrulline<br>proline<br>lysine | alanine<br>ornithine<br>citrulline<br>proline<br>glycine<br>arginine<br>histidine |

In view of the above variations in the amino acid metabolism in the living body after an operation, the composition of the amino acid infusion solution used after operations should preferably be such as to restore the normal amino acid pattern to the blood in order to compensate for the variations in the amino acid metabolism under the pathological conditions and to supply needed amount of amino acids or to balance the amino acid spectrum of the blood.

Suitable infusion compositions can be obtained by using the equation (1) below:

$$A_n = x_n / \Sigma x_n \times 100 \quad (1)$$

where $x_n = a_n^2 / b_n$, wherein $a_n$ stands for the normal value of an amino acid n, $b_n$ represents the post-operative value for the amino acid n and $A_n$ stands for the percentage of the amino acid n relative to the total amino acid in the infusion solution.

The composition of an amino acid infusion solution (S-0) as a 7% solution determined from equation (1) on the basis of the change in the amounts of amino acids in the blood of a rat that received an operation (Table 1) is shown in Table 4. When the solution (S-0) is administered intravenously to a rat which has had its small intestine resected, and the concentrations of the amino acids in the blood are measured, it can be shown that all of the amino acids are not restored to their normal levels in the blood. The reason is that the value for k, which stands for the homeostasis of plasma amino acid concentration, is different for each individual amino acid. Thus, the composition was modified for the amino acids that had not recovered to their normal levels, and a composition (S-1) thus obtained was injected continuously into a rat. The composition (S-1) was further modified for the amino acids that still had not recovered to their normal levels, and a new composition (S-2) was thus obtained. In a similar manner, the final composition (S-5) of the amino acid infusion solution capable of normalizing the amino acid concentrations in the blood after the operation was obtained, as shown in Table 4.

Table 4 also shows the ratios $k=A_n(S\text{-}5)/A_n(S\text{-}0)$ for the respective amino acids in the compositions (S-0) and (S-5). The value k represents the degree of homeostasis of the concentration of each amino acid in the blood. The larger the value of k, the less variability there is in the amino acid concentration in the blood upon administration thereof as an infusion solution. Among the amino acids which have larger k values are isoleucine, leucine, phenylalanine, tryptophan and valine with most of them being essential amino acids. Among the amino acids which have k values less than unity (1) are tyrosine, alanine, glutamic acid, glycine, proline and serine with most of them being nonessential amino acids. The k values for the nonessential amino acids are smaller because they may also be synthesized in the body.

A composition which is capable of normalizing the changes in the amino acid concentration in the blood of post-operative patients may be obtained in the following manner from composition (S-5) as obtained from the above experiments on the rats.

As described hereinabove, the changes in the amino acid concentrations in human blood after an operation are qualitatively similar to those observed in rats. A composition (H-0) shown in Table 5 which can restore the normal amino acid concentrations in the blood for a man after an operation was obtained from the normal values and by using equation (1). However, a factor which represents homeostasis is not included in composition (H-0), as in the case of composition (S-0) for the rat. Thus, by using the coefficient of homeostasis $k=A_n(S\text{-}5)/A_n(S\text{-}0)$ shown in Table 4, a composition (H-5) that would normalize the plasma amino acid concentrations of post-operative patients was obtained. The ratio of the respective amino acids for the composition (H-5) can be obtained by using equation (2) shown below:

TABLE 4

| AMINO ACID COMPOSITIONS OF S-0 AND S-5 (Weight %) | | | |
|---|---|---|---|
| Amino acids | S-0 | S-5 | K = 5/S-0 |
| isoleucine | 1.24% | 5.69% | 4.59 |

TABLE 4-continued

| AMINO ACID COMPOSITIONS OF S-0 AND S-5 (Weight %) | | | |
|---|---|---|---|
| Amino acids | S-0 | S-5 | K = 5/S-0 |
| leucine | 1.81 | 14.09 | 7.66 |
| lysine | 16.72 | 15.55 | 0.93 |
| methionine | 1.61 | 2.97 | 1.84 |
| phenylalanine | 1.28 | 6.74 | 5.27 |
| tryptophan | 1.11 | 4.58 | 3.69 |
| valine | 2.53 | 7.24 | 2.86 |
| threonine | 5.04 | 3.94 | 0.78 |
| cystine | 0.10 | 5.54 | 55.4 |
| tyrosine | 1.78 | 0.34 | 0.19 |
| alanine | 14.16 | 3.37 | 0.24 |
| arginine | 5.23 | 8.22 | 1.57 |
| aspartic acid | 0.38 | 0.44 | 1.16 |
| glutamic acid | 6.63 | 1.70 | 0.26 |
| glycine | 17.18 | 9.33 | 0.54 |
| histidine | 1.15 | 2.86 | 2.49 |
| proline | 7.78 | 4.42 | 0.57 |
| serine | 14.25 | 2.99 | 0.21 |

$$B_n = \frac{y_n}{\sum_n y_n} \times 100 \qquad (2)$$

$$\text{where } y_n = k \times k_n = \frac{A_n(S-5)}{A_n(S-0)} \times k_n,$$

wherein $k_n$ represents the percentage by weight of an amino acid n in composition (H-0) and $B_n$ represents the percentage by weight of the amino acid n in composition (H-5).

The weight percentages were converted into mole percent values to complete the tabulation of composition (H-5) in Table 5.

TABLE 5

| | H-0 (W/W%) | H-5 (W/W%) | H-5 (mole %) | the range of composition H-5 (mole % ± 5%) |
|---|---|---|---|---|
| isoleucine | 2.56 | 7.48 | 7.32 | 6.95–7.69 |
| leucine | 3.99 | 16.53 | 16.17 | 15.36–16.98 |
| lysine | 5.95 | 4.01 | 3.54 | 3.36–3.72 |
| methionine | 1.01 | 1.30 | 1.12 | 1.06–1.18 |
| phenylalanine | 2.03 | 10.78 | 8.41 | 7.99–8.83 |
| threonine | 5.79 | 7.53 | 8.15 | 7.74–8.56 |
| tryptophan | 1.78 | 2.85 | 1.80 | 1.71–1.89 |
| valine | 10.21 | 15.64 | 17.21 | 16.35–18.07 |
| cystine | 1.26 | 4.47 | 2.40 | 2.28–2.52 |
| tyrosine | 2.75 | 0.37 | 0.26 | 0.25–0.27 |
| alanine | 23.75 | 3.07 | 4.44 | 4.22–4.66 |
| arginine | 4.42 | 7.15 | 5.29 | 5.03–5.55 |
| aspartic acid | 0.18 | 0.71 | 0.69 | 0.66–0.72 |
| glutamic acid | 2.37 | 0.48 | 0.42 | 0.40–0.44 |
| glycine | 9.52 | 7.10 | 12.19 | 11.58–12.80 |
| histidine | 2.45 | 4.88 | 4.05 | 3.85–4.25 |
| proline | 15.03 | 4.48 | 5.02 | 4.77–5.27 |
| serine | 4.92 | 1.19 | 1.46 | 1.39–1.53 |

The amino acid composition of the present invention has been determined from the above results.

The composition (H-5) thus obtained has the following characterisitics. First of all, the contents of the branched chain amino acids amount to 40.70 mole percent, and the ratio of valine:leucine:isoleucine is approximately 2:2:1. Second, the ratio of essential amino acids to nonessential amino acids is 1.97:1 (mole/mole). Third, the content of phenylalanine is relatively high and amounts to 8.41 mole percent, whereas those for alanine, glycine, aspartic acid and glutamic acid are rather low. An amino acid infusion solution having the above characteristics thus far is not known nor has it been utilized in the art.

While the infusion solution of the present invention has the characteristic composition described above, other known ways and techniques, which have been adopted for conventional amino acid infusion solutions, can also be adopted for the present composition.

The infusion solution of the present invention has a pH value in the range of 5.0 to 7.8, preferably in the range of 6.5 to 7.5, and a concentration by weight in the range of 3 to 15%, preferably in the range of 5 to 8%.

The amino acids employed in the present invention may be used in free form, or as salts of such metals as sodium and calcium, or as salts of such mineral acids as hydrochloric acid and sulfuric acid or of organic acids such as acetic acid and malic acid. Alternatively, the amino acids employed in the present invention may be used in the form of amino acid derivatives which include such N-acetyl derivatives as N-acetyl-L-tyrosine, or in the form of salts of two amino acids or peptides of the same or different amino acids such as glycyl-L-tyrosine. In this case, the amounts of the respective amino acids that constitute the derivatives should naturally be included in the calculation of the composition ratio characteristic of the present invention.

It should be observed that a portion of all of the cystine can be substituted by cysteine and/or methionine, whereas a portion or all of the tyrosine can be substituted by phenylalanine.

Since the invention infusion solution is administered to a patient by intravenous injection, admixture of impurities such as harmful metal ions in the solution should be precluded. However, no specific limitations are placed on the addition of isotonic agents, stabilizers, pH controlling agents and other agents which are necessary for infusion solutions or other water soluble nutrients.

The infusion solution of the present invention can be prepared without any special difficulties and by application of any process known for preparing conventional amino acid infusion solutions. Thus, for instance, the amino acids of the present invention may be dissolved homogeneously in water so that the composition ratios as defined above can be obtained.

Having generally described this invention, a further understanding can be obtained by reference to certain specific examples which are provided herein for purposes of illustration only and are not intended to be limiting unless otherwise specified.

EXAMPLE 1

L-isoleucine, L-leucine, L-lysine, L-methionine, L-phenylalanine, L-threonine, L-tryptophan, L-valine, L-cysteine, L-tyrosine, L-alanine, L-arginine, L-aspartic acid, L-glutamic acid, glycine, L-histidine, L-proline and L-serine were dissolved in sterilized water while stirring the solution to homogeneity and achieving the composition ratios shown below. Acetic acid was added to the resulting aqueous solution of amino acids to adjust the same to a pH of 7.0. The resulting aqueous solution was subjected to milipore filtration and charged under nitrogen gas into a vessel for an infusion solution. The product infusion solution was obtained by autoclaving under the usual conditions.

| Amino Acids | W/V % | mmole/100 ml |
|---|---|---|
| L-isoleucine | 0.52 | 3.95 |
| L-leucine | 1.16 | 8.80 |
| L-lysine acetic acid salt | 0.40 | 1.94 |
| L-methionine | 0.09 | 0.60 |
| L-phenylalanine | 0.75 | 4.54 |
| L-threonine | 0.53 | 4.45 |
| L-tryptophan | 0.20 | 0.98 |
| L-valine | 1.09 | 9.30 |
| L-cysteine . HCl . $H_2O$ | 0.45 | 0.09 |
| L-tyrosine | 0.03 | 0.17 |
| L-alanine | 0.21 | 2.36 |
| L-arginine | 0.50 | 2.87 |
| L-aspartic acid | 0.05 | 0.38 |
| L-glutamic acid | 0.03 | 0.20 |
| glycine | 0.50 | 6.66 |
| L-histidine | 0.34 | 2.19 |
| L-proline | 0.31 | 2.69 |
| L-serine | 0.08 | 0.76 |
| Total of Amino Acids | 7.24% | |

EXAMPLE 2

By using the method described in Example 1, the following amino acids were used to obtain an infusion solution having the following composition ratios. Cystine was used in this example in place of cysteine which was used in Example 1.

| Amino Acids | W/V % | mmole/100 ml |
|---|---|---|
| L-isoleucine | 0.52 | 3.95 |
| L-leucine | 1.16 | 8.80 |
| L-lysine acetic acid salt | 0.43 | 2.09 |
| L-methionine | 0.33 | 2.21 |
| L-phenylalanine | 0.81 | 4.90 |
| L-threonine | 0.56 | 4.70 |
| L-tryptophan | 0.21 | 1.03 |
| L-valine | 1.09 | 9.30 |
| L-cystine | 0.10 | 0.42 |
| L-tyrosine | 0.03 | 0.17 |
| L-alanine | 0.23 | 2.58 |
| L-arginine | 0.54 | 3.10 |
| L-aspartic acid | 0.05 | 0.38 |
| L-glutamic acid | 0.04 | 0.27 |
| glycine | 0.53 | 0.71 |
| L-histidine | 0.37 | 2.38 |
| L-proline | 0.34 | 2.19 |
| L-serine | 0.09 | 0.86 |
| Total of Amino Acids | 7.43% | |

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. An amino acid based nutritional solution for intravenous administration, comprising an aqueous solution of the following amino acids:

| | Mole % |
|---|---|
| L-isoleucine | 6.95–7.69 |
| L-leucine | 15.36–16.98 |
| L-lysine | 3.36–3.72 |
| L-methionine | 1.06–1.18 |
| L-phenylalanine | 7.99–8.83 |
| L-threonine | 7.74–8.56 |
| L-tryptophan | 1.71–1.89 |
| L-valine | 16.35–18.07 |
| L-cystine | 2.28–2.52 |
| L-tyrosine | 0.25–0.27 |
| L-alanine | 4.22–4.66 |
| L-arginine | 5.03–5.55 |

-continued

|  | Mole % |
|---|---|
| L-aspartic acid | 0.66–0.72 |
| L-glutamic acid | 0.40–0.44 |
| glycine | 11.58–12.80 |
| L-histidine | 3.85–4.25 |
| L-proline | 4.77–5.27 |
| L-serine | 1.39–1.53 |

2. An amino acid based nutritional solution for intravenous administration, comprising an aqueous solution of the following amino acids:

|  | Mole % |
|---|---|
| L-isoleucine | 6.95–7.69 |
| L-leucine | 15.36–16.98 |
| L-lysine | 3.36–3.72 |
| L-methionine | 1.06–1.18 |
| L-phenylalanine | 7.99–8.83 |
| L-threonine | 7.74–8.56 |
| L-tryptophan | 1.71–1.89 |
| L-valine | 16.35–18.07 |
| L-cystine | 2.28–2.52 |
| L-tyrosine | 0.25–0.27 |
| L-alanine | 4.22–4.66 |
| L-arginine | 5.03–5.55 |
| L-aspartic acid | 0.66–0.72 |
| L-glutamic acid | 0.40–0.44 |
| glycine | 11.58–12.80 |
| L-histidine | 3.85–4.25 |
| L-proline | 4.77–5.27 |
| L-serine | 1.39–1.53 | wherein a portion or all of the cystine component is replaced by cysteine and/or methionine.

3. An amino acid based nutritional solution for intravenous administration, comprising an aqueous solution of the following amino acids:

|  | Mole % |
|---|---|
| L-isoleucine | 6.95–7.69 |
| L-leucine | 15.36–16.98 |
| L-lysine | 3.36–3.72 |
| L-methionine | 1.06–1.18 |
| L-phenylalanine | 7.99–8.83 |
| L-threonine | 7.74–8.56 |
| L-tryptophan | 1.71–1.89 |
| L-valine | 16.35–18.07 |
| L-cystine | 2.28–2.52 |
| L-tyrosine | 0.25–0.27 |
| L-alanine | 4.22–4.66 |
| L-arginine | 5.03–5.55 |
| L-aspartic acid | 0.66–0.72 |
| L-glutamic acid | 0.40–0.44 |
| glycine | 11.58–12.80 |
| L-histidine | 3.85–4.25 |
| L-proline | 4.77–5.27 |
| L-serine | 1.39–1.53 | wherein a portion or all of the tyrosine component is replaced by phenylalanine.

* * * * *